(12) United States Patent
Simpson

(10) Patent No.: US 8,122,809 B2
(45) Date of Patent: Feb. 28, 2012

(54) BALLOON WITH DIVIDING FABRIC LAYERS AND METHOD FOR BRAIDING OVER THREE-DIMENSIONAL FORMS

(75) Inventor: Charles L. Simpson, Westlake Village, CA (US)

(73) Assignee: C.R. Bard, Inc., Murray Hill, NJ (US)

( * ) Notice: Subject to any disclaimer, the term of this patent is extended or adjusted under 35 U.S.C. 154(b) by 372 days.

(21) Appl. No.: 12/517,450

(22) PCT Filed: Dec. 17, 2007

(86) PCT No.: PCT/US2007/087815
§ 371 (c)(1),
(2), (4) Date: Jun. 3, 2009

(87) PCT Pub. No.: WO2008/076992
PCT Pub. Date: Jun. 26, 2008

(65) Prior Publication Data
US 2010/0010438 A1    Jan. 14, 2010

Related U.S. Application Data

(60) Provisional application No. 60/870,479, filed on Dec. 18, 2006.

(51) Int. Cl.
*D04C 1/00* (2006.01)
(52) U.S. Cl. .................................. 87/11; 87/13
(58) Field of Classification Search ............. 87/11, 13; 606/192–196
See application file for complete search history.

(56) References Cited

U.S. PATENT DOCUMENTS

| | | | |
|---|---|---|---|
| 4,621,560 A | 11/1986 | Brown et al. | |
| 4,719,837 A * | 1/1988 | McConnell et al. | 87/1 |
| 4,881,444 A | 11/1989 | Krauland | |
| 4,885,973 A | 12/1989 | Spain | |
| 5,718,159 A | 2/1998 | Thompson | |
| 5,758,562 A | 6/1998 | Thompson | |
| 5,957,974 A | 9/1999 | Thompson et al. | |
| 6,019,786 A | 2/2000 | Thompson | |
| 6,622,604 B1 * | 9/2003 | Chouinard et al. | 87/11 |
| 6,746,425 B1 | 6/2004 | Beckham | |
| 7,309,324 B2 | 12/2007 | Hayes et al. | |
| 7,311,031 B2 * | 12/2007 | McCullagh et al. | 87/8 |
| 7,354,419 B2 | 4/2008 | Davies, Jr. et al. | |

(Continued)

FOREIGN PATENT DOCUMENTS
WO    WO 2008/063782    5/2008

OTHER PUBLICATIONS

"Braiding," 2005 Advanced Composite Materials & Textile Research Laboratory, University of Massachusetts-Lowell, <http://m-5.uml.edu/acmtrl/research-braiding.htm>.

(Continued)

*Primary Examiner* — Shaun R Hurley
(74) *Attorney, Agent, or Firm* — King & Schickli, PLLC

(57) ABSTRACT

A medical balloon with a variable diameter that is reinforced with continuous fibers woven to form a fabric with a varying number of layers and fiber densities. Portions of the balloon having a relatively smaller diameter are reinforced with a fabric having a reduced fiber density and an increased number of layers to facilitate the placement of the layers. The fabric also includes a braiding pattern that facilitates the transition from a single layer fabric to a multiple layer fabric. Also described is a manufacturing method for the braiding and layering.

20 Claims, 4 Drawing Sheets

U.S. PATENT DOCUMENTS

| | | | |
|---|---|---|---|
| 7,500,982 | B2 | 3/2009 | Pepper |
| 7,544,201 | B2 | 6/2009 | Pepper |
| 7,682,335 | B2 | 3/2010 | Pepper et al. |
| 7,914,487 | B2 | 3/2011 | Davies, Jr. et al. |
| 8,002,744 | B2 | 8/2011 | Pepper et al. |
| 2003/0153973 | A1* | 8/2003 | Soun et al. ............ 623/1.16 |
| 2004/0170782 | A1 | 9/2004 | Wang et al. |
| 2006/0085022 | A1 | 4/2006 | Hayes et al. |
| 2006/0130642 | A1* | 6/2006 | Tomich et al. ............ 87/9 |
| 2010/0185145 | A1 | 7/2010 | Pepper et al. |
| 2010/0243135 | A1 | 9/2010 | Pepper et al. |
| 2010/0318029 | A1 | 12/2010 | Pepper et al. |
| 2011/0082489 | A1 | 4/2011 | Davies, Jr. et al. |

OTHER PUBLICATIONS

"Engineered Non-Linear Elastic Blended Fabrics," NTC Project F00-PH05 2005, <http://www.ntcresearch.org/pdf-rpts/AnRp02/F00-PH05-A2.pdf>.

Guang-Wu Du, Tsu-Wei Chou, and P. Popper, "Analysis of three-dimensional textile preforms for multidirectional reinforcement of composites," J. Mater. Sci. 26 (1991) 3438-3448.

"3 Dimensional Braiding," <http://www.3tex.com/node/4>, current version available as early as May 24, 2010, but previous version available at least as early as PCT filing date of Dec. 17, 2007.

M. Dunn, E. Armstrong-Carroll, Y. Gowayed; "Engineered Non-linear Elastic Bland Fabrics," <http://www.ntcresearch.org/pdf-rpts/Bref0601/F00-P05.pdf>, Nov. 2002.

W. Seneviratne, J. Tomblin, "Design of a Braided Composite Structure With a Tapered Cross-Section," National Institute for Aviation Research Wichita State University Wichita, KS 64206-0093, May 2002.

The Department of Defense Handbook Composite Materials Handbook vol. 2, "Polymer Matrix Composites Materials Properties," <http://www.lib.ucdavis.edu/dept/pse/resources/fulltext/HDBK17-2F.pdf>, Jun. 17, 2002.

* cited by examiner

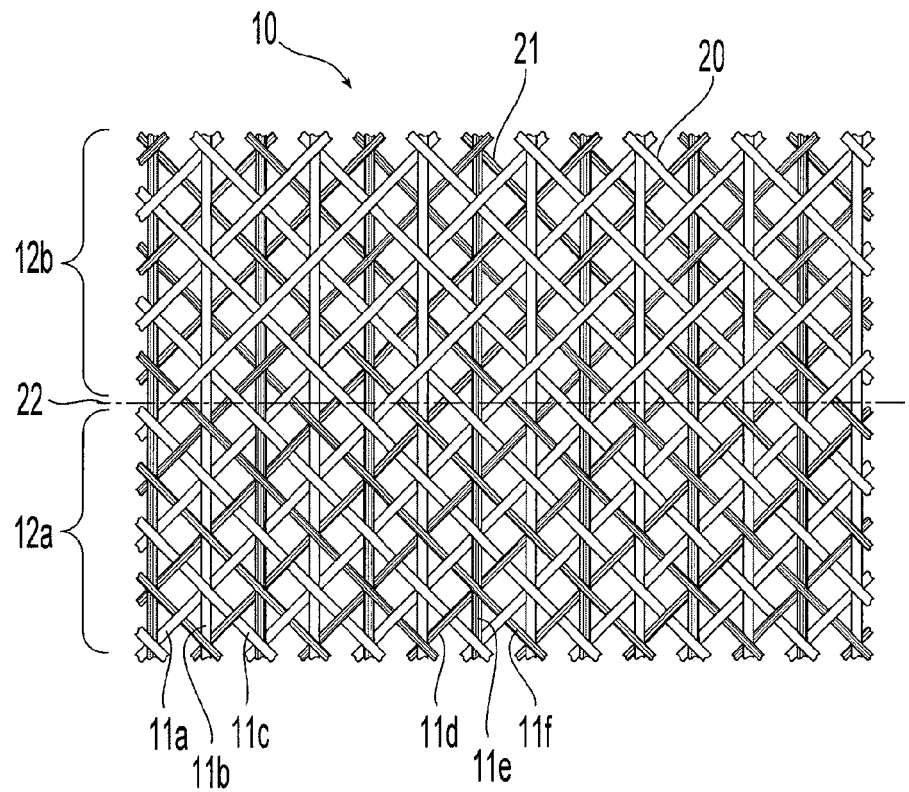
Fig. 1A
Fig. 1B
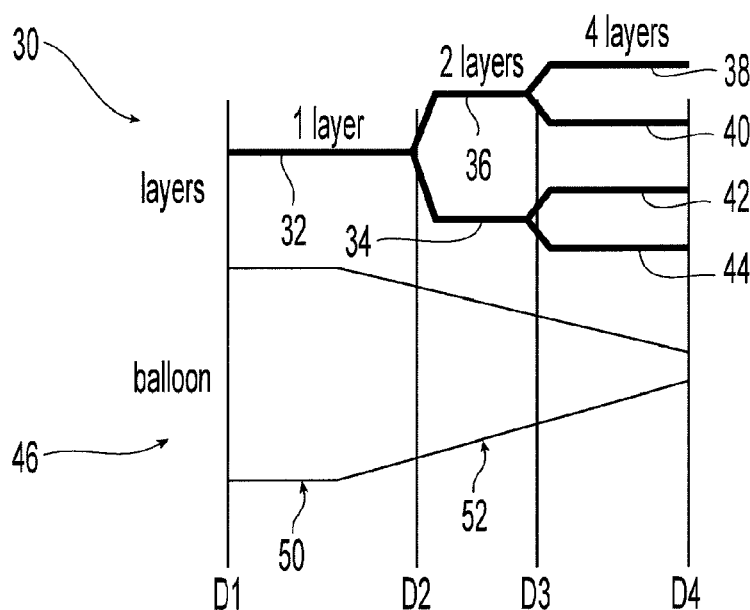
Fig. 2

BALLOON WITH DIVIDING FABRIC LAYERS AND METHOD FOR BRAIDING OVER THREE-DIMENSIONAL FORMS

PRIORITY DATA AND INCORPORATION BY REFERENCE

This application claims benefit of priority to U.S. Provisional Patent Application No. 60/870,479 filed Dec. 18, 2006 which is incorporated by reference in its entirety.

TECHNICAL FIELD

The present invention relates to methods and apparatus for braiding fibers over three-dimensional shapes. In particular, the invention relates to the reinforcement of balloons with weaved fibers and fabrics.

BACKGROUND ART

In the medical balloon art, medical balloons have been reinforced by placing fibers into pre-determined arrangements using manual or partially automated processes, as described in U.S. Pat. No. 6,746,425, which is incorporated by reference in its entirety. Some manual and partially automated manufacturing processes require the manual manipulation of fibers to properly dispose the fibers in the desired location of the balloon. The non-automated aspects of such processes increase the cost and time investment to manufacture a reinforced medical balloon as compared to highly automated processes. Also, the non-automated aspects of such processes, and the time associated with manual processes, prevent or impede the formation or efficient disposition of complex fiber patterns, or the formation of complex weave patterns that facilitate the disposition of a two-dimensional fabric over a three-dimensional contour associated with a medical balloon. It is also believed that automated processes facilitate a more precise and consistent disposition of fibers that is either impossible or difficult to achieve with manual or partially automated processes.

Braiding technologies and 2D and 3D braiding machines are described in: "Braiding," 2005 Advanced Composite Materials & Textile Research Laboratory, University of Massachusetts-Lowell, available at the University of Massachusetts-Lowell's Advanced Composite Materials & Textile Research website. Braiding technologies and Cartesian braiding machines are described at the website of 3TEX, Inc. A report by the National Textile Center (NTC) of Springhouse, Pa., describes braiding patterns and describes the behavior of braids under tensile load, and the effect of yarn angle with respect to load and jamming condition, in "Engineered Non-Linear Elastic Blended Fabrics," NTC Project F00-PH05 2005. The following articles describe braids: Guang-Wu Du, Tsu-Wei Chou, and P. Popper, "Analysis of three-dimensional textile pre-forms for multidirectional reinforcement of composites," J. Mater. Sci. 26 (1991) 3438-3448; M. Dunn, E. Armstrong-Carroll, Y. Gowayed; "Engineered Non-linear Elastic Bland Fabrics"; W. Seneviratne, J. Tomblin, "Design Of A Braided Composite Structure With A Tapered Cross-Section," National Institute for Aviation Research Wichita State University Wichita, Kans. 67260-0093; and The Department Of Defense Handbook Composite Materials Handbook Volume 2, "Polymer Matrix Composites Materials Properties,". Braiding technology is also described in U.S. Pat. Nos. 5,718,159, 5,758,562, 6,019,786, 5,957,974, 4,881,444, 4,885,973, and 4,621,560. Each of the above-identified references are incorporated by reference herein.

For medical balloons, very thin walls are desirable. To reduce wall thickness, it is necessary to reduce the thickness of each fiber and increase the number of fibers to supplement for the reduced strength of the thinner fibers. If the thickness of the fibers is reduced, it is necessary to increase the number of fibers, and the fiber density, by the square of the reduction in thickness, in order to maintain the same tensile strength in the reinforced balloon wall. It is believed that the reduction of fiber thickness leads to a problem when the fibers are braided. This is because of the bunching or jamming effect that occurs when a continuous braided fabric is disposed over a cylindrical portion of a balloon and then continued over a portion of the balloon with a reduced diameter, such as when a fabric extends from a cylindrical balloon form to a conical end of the balloon. It is also believed that the same problem exists when a fabric is disposed over any three-dimensional object that reduces from one diameter to a smaller diameter.

At the conical end of a balloon, the fiber density increases as the diameter of the balloon decreases, as the same number of fibers are made to cover a decreasing circumferential area. If the weave pattern is changed to allow for a lower fiber density at the areas of reduced diameter, the wall thickness can become too thin and a transition to a different fiber angles in the weave can cause the fibers to bunch or jam and prevent further reduction in balloon diameter. Also, sparse braiding provides for greater spacing between fibers and thereby increase the jamming angle between fibers, and wall thickness is sacrificed in the main part of the balloon because of the inverse square relationship between the wall thickness and the fiber density required to achieve a constant wall strength. In other words, the fibers need to get thicker to maintain the reinforced strength per unit area of the balloon wall. As a result, the fiber density limitation at the balloon ends dictates a sub-optimal fiber density—and concomitant wall-thickness—over the central region of the balloon where the diameter is largest.

DISCLOSURE OF INVENTION

A structure and method for making a fiber-reinforced balloon for medical treatments such as percutaneous transluminal coronary angioplasty (PTCA), and delivery of a vascular stents or stent grafts, that is amenable to automated manufacture and that permits fiber angles to be optimized for holding pressure.

In the embodiments described herein, a continuous fiber wind is weaved to make a fabric that reinforces a balloon with a varying diameter while minimizing jamming of the fabric as the fabric transitions from covering a large diameter portion of the balloon to a smaller diameter portion of the balloon. A braiding pattern is used that transitions from a single layer to multiple layers as the fabric transitions to smaller diameter portions of the balloon. When the single layer fabric transitions to a multiple layer fabric, the fiber density of the single layer fabric is reduced in each of the multiple layers as each fiber of the single layer is directed to one of the multiple layers. When two or more layers are formed from a single layer, the fiber density of the innermost reinforcing later of the balloon can be controlled to minimize jamming or bunching of the woven fabric. The fiber densities of the layers formed proximate to the innermost layer, when the innermost layer is formed, can also be controlled to permit the composite layering of the balloon as the diameter of the balloon decreased. The dividing of the single layer fabric into multiple layers thus facilitates a balloon to be reinforced with fibers that extend across the entire balloon and into portions of the balloon with variable diameters, thereby facilitating the automated fabrication of a reinforced balloon. The dividing of a single layer also facilitates disposition of multiple reinforcement layers at reduced diameter portions of a balloon with minimized bunching of fabrics due to increased fiber density.

In one embodiment, the medical balloon includes first and second fibers that together define a main fabric layer that reinforces a main portion of the balloon, with the first fibers defining a first fabric layer that reinforces a first portion of the balloon and the second fibers defining a second fabric layer that reinforces the first portion of the balloon, and with the first fiber layer separate from and disposed adjacent to the second fiber layer.

In another embodiment, the medical balloon includes first and second fibers that at least in part interweave together to define a main layer that reinforces a main portion of the balloon, with the first fibers defining a first layer that reinforces a first portion of the balloon, with the second fibers defining a second layer that reinforces the first portion of the balloon, and with the first fiber layer separate from and disposed adjacent to the second fiber layer.

In yet another embodiment, the medical balloon includes a main fabric layer reinforcing the balloon, a first fabric layer contiguous with and extending from the main fabric layer to reinforce the balloon, and a second fabric layer contiguous with and extending from the main fabric layer to reinforce the balloon, with the first fabric layer disposed separate from and adjacent to the second fabric layer.

In still another embodiment, the medical balloon includes a main fabric having a main braid pattern of interweaved first and second fibers that reinforce the balloon, a first fabric having a first braid pattern of the first fibers, and a second fabric having a second braid pattern of the second fibers, with the first and second fibers joining the main fabric to the first and second fabrics.

In another embodiment, the medical balloon includes a central section of the balloon with a first outer diameter, a tapering end of the balloon with a second outer diameter that is less than the first outer diameter, a main fabric with interweaved first and second fibers and with the main fabric disposed on a the central section of the balloon, a first fabric having only interweaved first fibers disposed on the tapering end, and a second fabric having only interweaved second fibers disposed over the first fabric.

In each of the above-described embodiments, the first fabric, layer, or fabric layer can separate into an inner first fabric, layer, or fabric layer and an outer first fabric, layer, or fabric layer to reinforce the balloon. The second fabric, layer, or fabric layer can be separated into an inner second fabric, layer, or fabric layer and an outer second fabric, layer, or fabric layer to reinforce the balloon. The main or central portion of the balloon can define a cylinder and the first, second, end, or tapering portions can define cones. The main fabric, layer, or fabric layer can also connect to the first and second fabric layers proximate to a transition between a cylindrical portion of the balloon and a cone section of the balloon. Also, each of the above-described embodiments can have the balloon engaging a catheter, the balloon engaging an implantable device disposed around the exterior of the balloon, and the balloon engaging a stent disposed around the exterior of the balloon.

Also, the method of manufacturing a medical balloon includes interweaving first and second fibers to weave a main fabric to reinforce a central section of the balloon, interweaving only the first fibers to weave a first fabric to reinforce a tapering end of the balloon having an outer diameter the is less than an outer diameter of the central section, and interweaving only the second fibers to weave a second fabric to reinforce the tapering end of the balloon by disposing the second fabric over the first fabric. This method can include weaving the first fibers to form an inner first fabric and an outer first fabric to reinforce the tapering end of the balloon, weaving the second fibers to form an inner second fabric and an outer second fabric to reinforce the tapering end of the balloon, forming the central section of the balloon to define a cylinder and forming the tapering end of the balloon to define cones, and weaving the main fabric to join the first and second fabrics proximate to a transition between a cylindrical portion of the balloon and a cone section of the balloon.

The balloon and fibers are preferably polymers, and attached to the balloon base by an adhesive. Longitudinal fibers preferably run substantially parallel to the longitudinal axis of the balloon. The method preferably includes heating a thermopolymer to embed an longitudinal array of fibers in a matrix covering a tube. The method preferably also includes inflating an untwisted tube in a mold before winding hoop fiber and including heating a thermopolymer to embed the longitudinal array of fibers in a matrix covering the inflated tube.

According to yet another preferred embodiment, a method of forming a fiber reinforced balloon, comprises: holding an array of longitudinal fibers on the surface of a vessel to be reinforced while simultaneously wrapping a hoop fiber helically around the array of fibers to form a helix which crosses the longitudinal fibers at substantially right angles.

Preferably, the wrapping includes circling a bobbin, which holds the hoop fiber, around the vessel. The holding can be performed by an array of spring biased fiber feeders. The method preferably also includes applying a curable coating to the fibers after the wrapping and subsequently curing the curable coating to form an outer surface. The method preferably also includes applying an adhesive to the surface of the vessel prior to holding and wrapping.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 1A illustrates an exemplary braid pattern that transitions from one layer to two layers.

FIG. 1B schematically illustrates an edge on view of the braid pattern of FIG. 1A.

FIG. 2 schematically illustrates a fabric having a braid pattern that transitions from a single layer to multiple layers and a cross-sectional profile of an end of a balloon.

MODE(S) OF CARRYING OUT THE INVENTION

Figure 3:
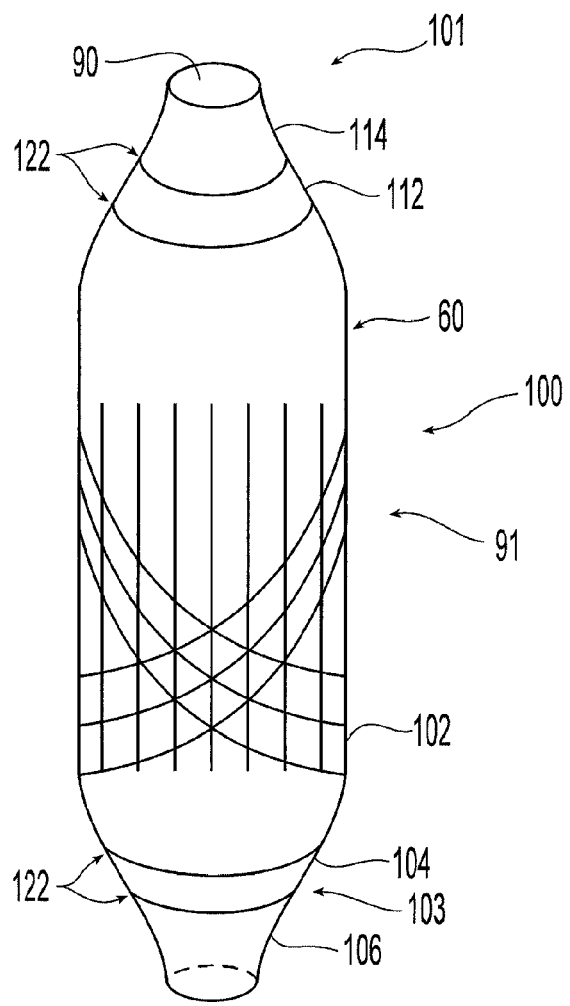
FIG. 3 is an isometric illustration of balloon reinforced with the braid pattern of FIGS. 1A, 1B, and 2C.

As illustrated in FIGS. 1A and 1B, an exemplary fabric 10 has a triaxial structure with fibers 11a, 11b, 11c, 11d, 11e, 11f disposed in three directions to form a braid of the fabric 10. Fibers 11a, 11b, 11c are illustrated without shading and fibers 11d, 11e, 11f are illustrated with shading. Fabric 10 has two portions: a single-layer portion 12a where the fibers 11a, 11b, 11c, 11d, 11e, 11f are interwoven to form the fabric 10 with a single layer 18, and a two-layer portion 12b where the fibers 11a, 11b, 11c are interwoven to form a first layer 20 of the fabric 10 and the fibers 11d, 11e, 11f are interwoven together to form a second layer 21 of the fabric 10. As also illustrated in FIG. 1A, it can be seen that layers 20 and 21 are identical in terms of the braid pattern and offset relative to each other.

The boundary where the fabric 10 transitions from the single-layer portion 12a to the two-layer portion 12b is a transition line 22. As can be appreciated from FIGS. 1A and 1B, the fiber density of the single-layer portion 12a is twice the fiber density of either layers 20 or 21. It can also be appreciated that the weave patterns of each of the first and second layers 20, 21 are disposed to continue without interruption the weave patterns established by the shaded and unshaded fibers in the single-layer portion 12a. The schematic side view in FIG. 1B shows, edge-on, how the first layer 20 and second layer 21 join to form the single layer 18 at the transition line 22. As can also be appreciated, the division of single layer 18 into first layer 20 and second layer 21 can be repeated by further dividing one or both of first and second layers 20, 21 into additional layers at additional transition lines. It can also be appreciated that the single-layer portion 12a can be divided into more than two layers by, for example, having the six fibers 11a-11f divide into three layers that each have two of the six fibers 11a-11f, or into six layers that each have one of the six fibers 11a-11f. It is also contemplated that the single-layer portion 12a could divide into layers that have a differing numbers of fibers, such as a first layer with four of the six fibers 11a-11f and a second layer with two of the six fibers 11a-11f.

FIG. 2 is a schematic illustrating multiple transitions in a fabric 30 from a single layer structure having a layer 32 to two-layer structure having a layer 34 and a layer 36, and then again having a transition in which layer 34 divides into layers 42, 44 and layer 36 divides into layers 38, 40 to form a four-layer structure of fabric 30.

As can be appreciated, the braiding pattern of fabrics 10, 30 may be constructed to follow a shape, such as the conical end of a medical balloon 46, as schematically illustrated in FIG. 2. Balloon 46 can have a diameter that decreases progressively from diameter D1 over a cylindrical portion 50 of the balloon 46 to a range of smaller diameters such as diameters D2, D3, D4 in a conical portion 52 of the balloon 46. The diameters D2, D3, D4 mark transition lines 22 where a layer divides into two layers, such as where layer 32 branches into layers 34, 36. The transition lines 22 can follow other balloon diameters and shapes using the same layer division mechanism to control the density of the yarns in each layer. The transition lines 22 can also be disposed in a balloon with varying geometries, such as a balloon with a cylindrical portion 50 having a portion with a diameter that is less than diameter D1, or with protrusions extending from the balloon, or with other features that vary the cross-sectional shape and dimensions of the balloon. Also note that although the embodiments discussed herein focus on balloons, the braiding and layer dividing technique described herein can be applied to other kinds of structures, including non-pressure holding structures such as stents, grafts, or composite articles of manufacture.

As shown in FIGS. 1A-2, when the same fibers 11a-11 if are divided among multiple layers, the fiber density per layer is reduced, which allows the braid of the fabric of each layer to conform to a smaller diameter of the balloon without causing the fibers or layers to bunch or jam due to the decreasing circumferential area of the balloon. For example, the fabric 30 can be wrapped over a structure with a reducing diameter, such as at conical portion 52, without causing the fibers of each layer in the fabric 30 to bunch up or create an undesirably high fiber density at smaller diameters. The exemplary braiding and layer dividing technique described herein thus advantageously allows for a fabric with a single continuous braid structure to be formed over an entire balloon while aligning the braid fibers in a preferable geodesic arrangement. The exemplary dividing technique also facilitates the control of fiber density and the arrangement of layers when the fabric is disposed in a variety of shapes such as, for example, a conical section 52 having a saddle (S-shaped, serpentine, or hyperboloid profile) or spheroidal shape.

FIG. 3 illustrates a balloon 100 with a balloon base 90 having a fabric 60 with a single layer region 102 disposed in a central cylindrical portion 91 of the balloon 100 and including a portion of tapered regions 101, 103, and double layer regions 104, 112 disposed in each of the tapered regions 101, 103, respectively. Quadruple layer regions 106, 114 extend toward the extreme ends of the balloon 100 at the tapered portions 101, 103.

Figure 4:
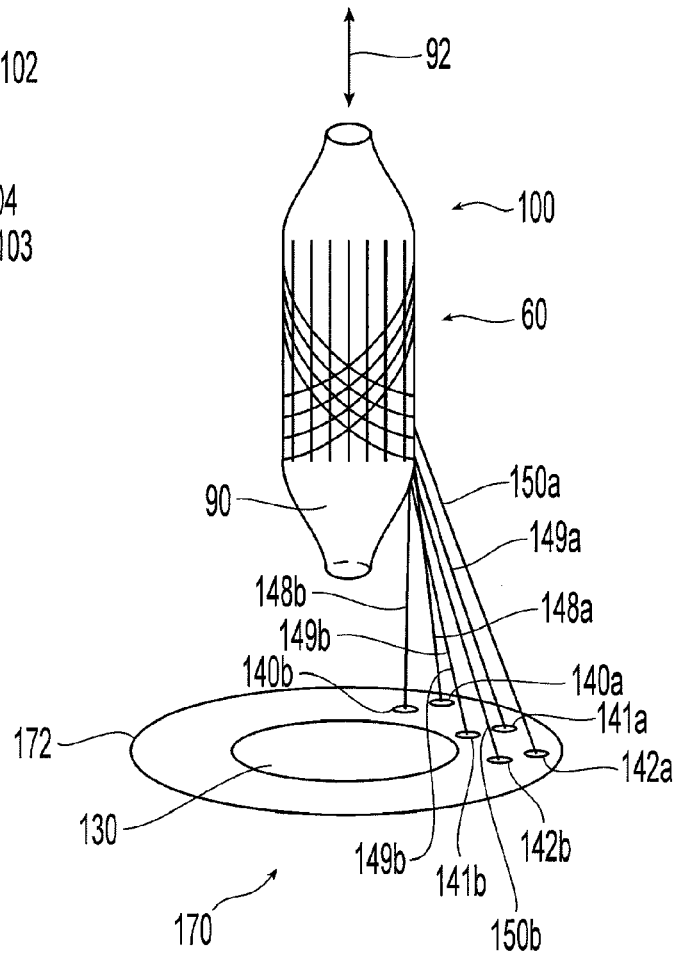
FIG. 4 illustrates device for forming a braid pattern of a fabric on a three-dimensional surface of a balloon.

A preferred method of forming a braid of a fabric which transitions from single to multiple layers is schematically represented in FIG. 4. A braiding machine 170 has floating bobbins 140a, 140b, 141a, 141b, 142a, 142b each controlling the disposition of fibers 148a, 148b, 149a, 149b, 150a, 150b. The bobbins are moved by a conveyor table 172 which is preferably a Cartesian-type braiding machine employing a Cartesian braiding process. A Cartesian braiding process is capable of producing multiple layer or single layer braids of any desired braid structure and allows the formation of the braid structure to change as the fabric is being made, i.e., on the fly. Generally the preferred braid structures are laid out in a two dimensional pattern over a three-dimensional surface and capable of changing as the braid structure extends in an axial direction 92 of the fabric 60, balloon base 90, or balloon 100. The braiding machine 170 moves the bobbins 140a, 140b, 141a, 141b, 142a, 142b on a machine bed (not shown) according to a preset program that permits the creation of transition lines 122 where the layering of the fabric 60 changes between single layer region 102, double layer regions 102, 114, and quadruple layer regions 106, 114. Bobbin-passing mechanisms (not shown) shuttle the bobbins 140a, 140b, 141a, 141b, 142a, 142b around a planar array (not shown) to allow the bobbins to pass around each other in such a manner as to create the braid, and to create transition lines 122. Six bobbins 140a, 140b, 141a, 141b, 142a, 142b are shown in the drawing although a fewer or greater number of bobbins can be used to form a fabric with a variety of braid structures.

Note that although the term "Cartesian" is used, this is not intended to limit the preferred method and apparatus for making the braid to ones in which the bobbins follow rectilinear paths or rectilinear arrays of stations. For example, for balloons with round cross-sections, it may desirable for the bobbin transferring mechanisms to define polar arrangements of bobbin passing mechanisms. So it should be understood that Cartesian-type braiding machines, as the characterization is used herein, may encompass any type of bobbin-passing device. Also note that the braid may be formed by mechanisms other than such a Cartesian-type device.

In a Cartesian-type braiding machine 170, fibers 148a, 148b, 149a, 149b, 150a, 150b are disposed on balloon base 90 in a braiding pattern that transitions from a single layer to multiple layers by moving three bobbins 140a, 141a, 142a around the circular conveyor table 172 in any desirable sequence to form a first braided layer corresponding to first layer 20 on the base balloon 90. Bobbins 140*b*, 141*b*, 142*b* are also moved around conveyor table 172 to form another a second braided layer corresponding to second layer 21 on the base balloon, possibly over the first layer 20, so that the fibers 148*b*, 149*b*, 150*b* do not interweave with fibers 148*a*, 149*a*, 150*a*. Two separate braided layers are thus formed. The balloon base 90 is also moved relative to the conveyor table 172 as the braided layers are progressively formed and, when the transition line 122 is to be formed, the bobbins 140*a*, 140*b*, 141*a*, 141*b*, 142*a*, 142*b* move to cause the first braided layer and the second braided layer with be interwoven to form a single braided layer corresponding to single layer 18. The reverse of this process can be performed as well, with the fabric 60 transitioning from a single braided layer to multiple braided layers. A varying number of layers can be formed with a suitable number of bobbins and a sufficient array of trajectories for the bobbins to follow.

The trajectory of the fibers may be controlled by controlling the feed rate of the balloon base 90 relative to the movement of the bobbins, as is known in the art of Cartesian and other types of braiding systems. Note that although a cylindrical structure having the form of a medical balloon is shown by way of example, other shapes of balloons or other structures can be reinforced using the structures and methods described.

One type of mechanism for moving the bobbins employs rotating elements that are fixed at an array of stations, and the rotating elements have recesses that pass the bobbins from station to station. Bobbins can be programmed to move in any course over the whole plane of the conveyor plane 172. If correspondingly programmed, a single braided layer can be made to transition to a two braided layers without any interruption. The bobbin-passing mechanism of the Cartesian braiding machine can be formed with a hole 130 in the center of conveyor table 172 to allow a cylindrical mandrel (not shown) to pass through and facilitate the weaving of the braided layers around the mandrel.

Circular looms and other automated fabric manufacturing techniques pose problems for high performance thin-walled structures such as medical balloons. It is believed that it can be difficult to form a helical or longitudinal fiber pattern over a balloon base or mandrel with a varying cross-section. It is also believed that looms that require a shuttle bobbin cannot be used with a varying balloon base or mandrel cross-section without the use of a complex mechanism to pass the shuttle bobbin and an additional device to perform a beater function of densifying the weft yarns. Also, friction between fibers can cause problems, particularly when the fibers are very thin. It is also believed that braiding is made difficult when there is a need for weaving, managing variations in the balloon base or mandrel diameter, and maintaining geodesic yarn trajectories.

It is believed that placing fibers without interweaving overcomes some of the difficulties associated with weaving and braiding found in existing techniques. Fibers may be aligned in the longitudinal and hoop directions to avoid problems with respect to geodesic alignment and circular looms. The exemplary dividing technique and layering also has the advantage of limiting friction during manufacturing because friction between fibers is reduced because few fibers are interlaced with each other to form the fabric. Also, smoother trajectories followed in a non-woven arrangement is believed to enhance strength and reduce stretch of the fabric.

Figures 5A, 5B:
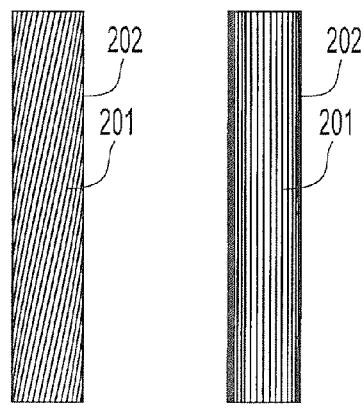
FIGS. 5A through 5E illustrate exemplary manufacturing steps for forming a nonwoven or woven fiber-reinforced fabric for a balloon.

Another method for making a balloon with fibers is illustrated in FIGS. 5A-5D. As shown in FIG. 5A, a tube 202 is wrapped helically with fibers 201. The surface of the tube 202 is preferably first coated with an adhesive. The tube 202 is preferably of a material that has low elasticity in the axial direction of the tube so as to stretch primarily in the circumferential direction. Also, prior to wrapping the fibers 201, the tube 202 is preferably twisted a predetermined distance about its longitudinal axis such that an elastic torsion is generated within the wall of the tube 202. It is believed that a tube made of a material with anisotropic elastic properties and formed so as to be inelastic along its longitudinal axis will tend to shorten when twisted in a circumferential direction about the longitudinal axis of the tube. When the tube 202, with the fibers adhered thereto, is subsequently untwisted as shown in FIG. 5B, the fibers 201 become aligned with the longitudinal axis of the tube 202.

Figure 5C:
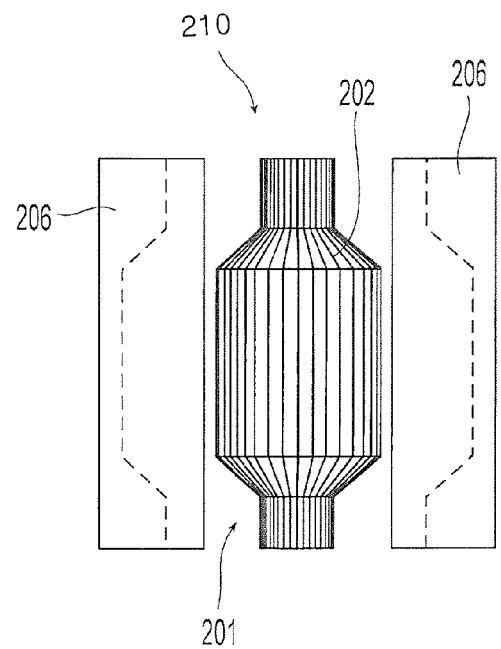

Referring to FIG. 5C, the tube 202 is thereafter expanded by inflation in a mold 206 that causes the tube 202 and attached fibers 201 to expand to form a reinforced balloon base 210. The tube 202 and fibers 201 are inelastic in the axial direction of the tube 202, which causes the length of tube 202 to shorten as it is circumferentially expanded in the mold 206 to form reinforced balloon base 210. The mold 206 may be lined with a thermopolymer before encapsulating the tube 202 within the mold 206 and the mold can be heated to facilitate the fixing of the fibers 201 to the thermopolymer coating. All or a portion of the tube 202 can be subsequently removed from the reinforced balloon base 210, or an internal mandrel to the tube 202, if used, can be removed if desired.

In alternative to the thermopolymer coating, any chemically curable plastic coating can be applied to the mold 206 recess so that the fibers 201 are pressed into the coating by the expansion of the tube 202 when forming the reinforced balloon base 210. Alternatively the mold 206 may have porous recesses that permit injection of a curable material into a space between the fibers 201 and the tube 202.

Figures 5D, 5E:
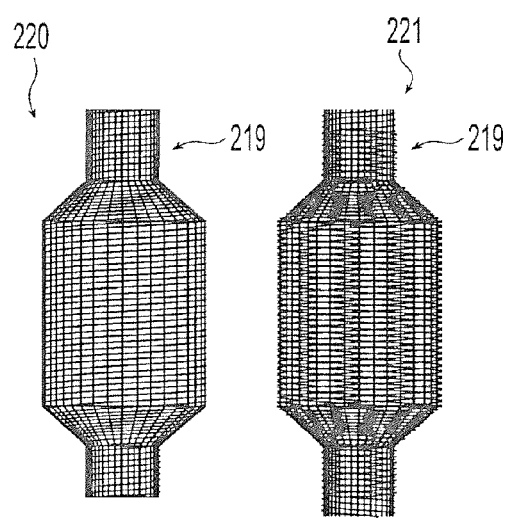

Once the reinforced balloon base 210 with longitudinally-disposed fibers 201 is formed, a helical wind 219 may be formed around the reinforced balloon base 210 by rotating the reinforced balloon based 210 and feeding a fiber over it tangentially from an axially advancing bobbin, to form balloon 220 as illustrated in FIG. 5D. Preferably, the reinforced balloon base 210 is first coated with a material to prevent the helical wind from slipping. In another embodiment, two helical winds 219 are applied to the reinforced balloon base 210 with symmetric helical angles relative to the longitudinal axis of the balloon or to each other, to form balloon 221 as illustrated in FIG. 5E. The two helical winds 219 can be disposed sequentially, without weaving, or simultaneously in a weaved pattern.

Preferably multiple balloons are created at once from a single long tube 202. The tube may be expanded into the mold 206 and advanced to create additional balloons 210 or multiple molds 206 may be supported in a longitudinal array to create multiple balloons 210 at once. A single helical wind can be created over multiple balloons 210 to achieve manufacturing economies over a single-balloon manual method.

Figure 6:
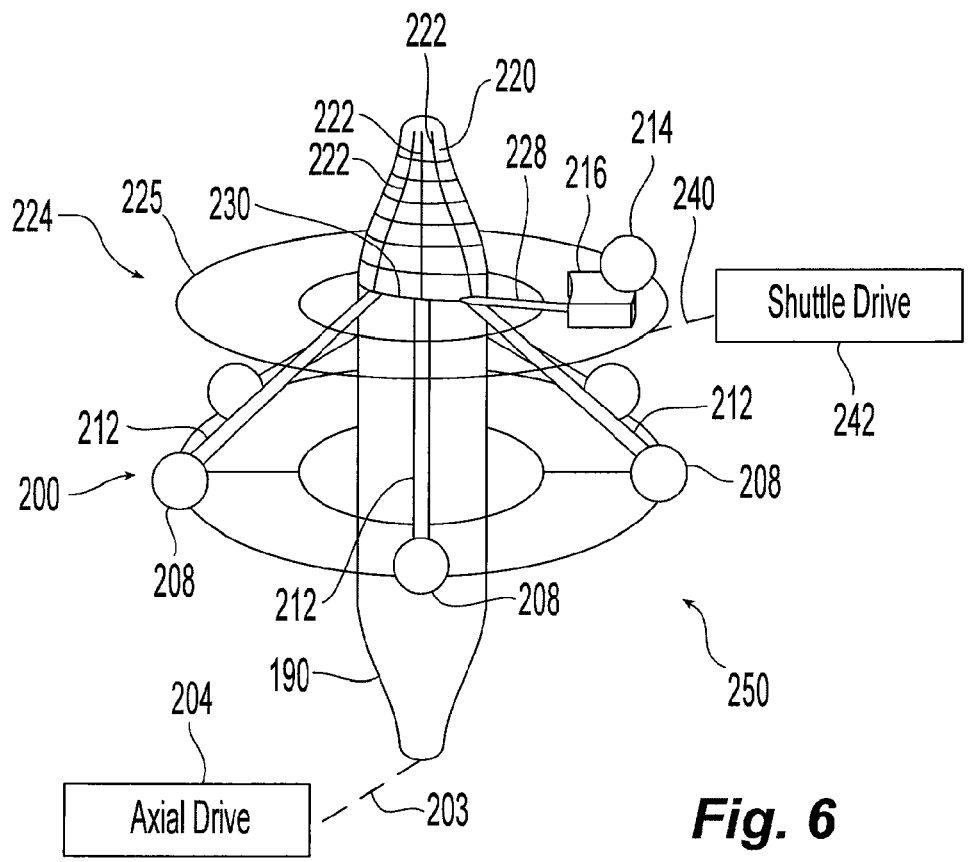
FIG. 6 illustrates an apparatus for disposing fibers on a mandrel or base structure.

FIG. 6 schematically illustrates a weaving device 250 for laying fibers over a mandrel or balloon base 190 to form balloon 220. The mandrel or balloon base 190 is moved through a longitudinal fiber feeder 200 in the weaving process by an axial drive 204 and axial drive transmission 203. The longitudinal fiber feeder 200 feeds longitudinal fibers 222 from longitudinal fiber spools 208 onto the mandrel or balloon base 190. At the same time, a helical fiber feeder 224 which orbits on a track 225 winds a helical fiber 230 in a weave with the longitudinal fibers 222 laid onto the mandrel or balloon base 190 by the longitudinal fiber feeder 200. A feeder support 228 stems from a shuttle 216 having a helical fiber spool 214 which is driven by a shuttle drive 242 and transmission 240 around the circular track 225. The mechanism for driving the shuttle 216 can be any suitable mechanism, such as is used for driving the shuttle of a circular loom. The fibers may be held in tension by feeder supports 212 for the longitudinal fibers 222, and by feeder support 228 for the helical fiber 230. The feeder supports 212, 228 can be tubes or guide wires or any suitable device for guiding the fibers as they unwind from the respective spools 208, 214.

The feeder supports 212 are arranged to follow the surface of the mandrel or balloon base 190 and are preferably positioned such that their tips are close to the mandrel or balloon base to position the longitudinal fibers 222 as it is laid onto the mandrel or balloon base 190. The curved surface of the mandrel or balloon base 190 is followed by the tips of the feeder supports 212 so that the longitudinal fibers 222 do not extend or bridge substantially to reach the surface of the mandrel or balloon base 190. The longitudinal fibers 222 are drawn as the mandrel or balloon base 190 moves axially relative to the longitudinal fiber feeders 200. Thus, as the mandrel or balloon base 190 advances, the longitudinal fibers 222 are laid in place and the helical fiber 230, which is spooled in a circumferential pattern and naturally drawn into a helix-shaped wind as the mandrel or balloon base 190 advances, holds the longitudinal fibers 222 in place against the surface of the mandrel or balloon base 190. Preferably, the mandrel or balloon base 190 is provided with a tacky or non-slip coating to prevent the helical wind from slipping off.

Figure 7:
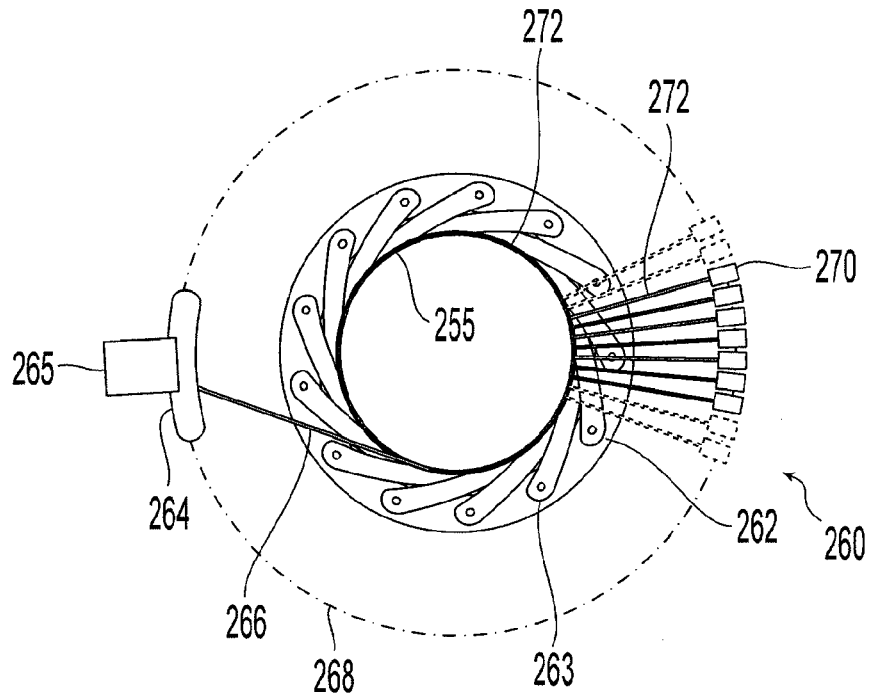
FIG. 7 illustrates an alternative apparatus for disposing fibers on a mandrel or base structure.

FIG. 7 shows a weaving device 260 similar to that of FIG. 6 from an end-facing point of view along the longitudinal axis of the weaving device 260. In this embodiment, the longitudinal fibers 272 are fed from multiple spools 270 which fully surround the mandrel or balloon base 255, though only a few are illustrated in FIG. 7. The weaving device 260 includes an iris 262 which circumferentially expands and contracts to maintain the position of the longitudinal fibers 272 close to the mandrel or balloon base 255. The iris 262 may be designed to passively control the position of the longitudinal fibers 272 with springs or biasing blades 263 the maintain contact with or a close proximity to the mandrel or balloon base 255. Alternatively the iris 262 may be configured by a suitable drive mechanism based on feedback from a mechanical or optical profile follower or made programmable by synchronizing the iris 262 with the movement of the mandrel or balloon base 255 having a predetermined profile. A helical fiber 266 is fed from a spool 265 on a shuttle 264 which circles the mandrel or balloon base 255 along a path of travel 268 as the mandrel or balloon base 255 is moved in the axial direction normal to the plane of FIG. 7. Various additional details of the described embodiments, such as how base balloons may be used or other various types of mandrels, are described in International Application No. PCT/U.S.07/81264, which is hereby incorporated by reference in its entirety herein as if fully set forth herein.

As described in International Application No. PCT/U.S.07/81264, a mold illustrated in FIGS. 7 and 8A-8C may be used to melt a matrix around fibers to form a balloon. In one method, the fibers are coated with a matrix-forming material that flows at a lower temperature than the base material of the fibers. For example high melting-temperature fibers may be coated with low melting-temperature thermoplastic. Then a pre-form may be formed either by braiding over a collapsible mandrel with the two-part fibers. The mandrel with the pre-form is then placed in the mold and heated to melt the low melting temperature material but leave the fibers intact. The mold is then removed and the mandrel can be collapsed or disintegrated to remove it, leaving the fully formed balloon with the spaces between the fibers filled with the low melting temperature material of the original fibers. The mandrel can be made of glass, metal, wax, or rigid or flexible polymer, for example, and removed by deflating or by dissolving with acid, for example.

As another alternative, the starting fibers could be a two-part fiber with one part, for example, a coating of a chemically hardenable or curable material. Instead of heating in the mold, the pre-form could be sprayed with a chemical hardener and molded until hardening occurs, as described in International Application No. PCT/US07/81264 at FIGS. 7 and 8A-8C. The mandrel could then be removed in a manner set forth in the previous embodiment.

Note that the proportions of the articles and precursors (parisons) shown in the figures are not intended to be representative of a practical medical balloon and are chosen for the purpose of illustration. While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

I claim:

1. A medical balloon, comprising:
    a central section of the balloon having a first outer diameter;
    a tapering end of the balloon having a second outer diameter that is less than the first outer diameter; and
    a plurality of continuous interwoven fibers disposed to form a fabric, wherein the fabric defines but a single layer on the central section and multiple layers on the tapering end.

2. A method of manufacturing a medical balloon, comprising:
    interweaving first and second fibers to weave a main fabric layer to reinforce a central section of the balloon;
    interweaving only the first fibers to weave a first fabric layer to reinforce a tapering end of the balloon having an outer diameter that is less than an outer diameter of the central section; and
    interweaving only the second fibers to weave a second fabric layer to reinforce the tapering end of the balloon by disposing the second fabric layer over the first fabric layer.

3. The method of claim 2, forming the central section of the balloon to define a cylinder, and forming the tapering end of the balloon to define cones.

4. The method of claim 2, weaving the main fabric layer to join the first and second fabric layers proximate to a transition between a cylindrical portion of the balloon and a cone section of the balloon.

5. A medical balloon having a variable diameter, comprising:
    a plurality of first and second fibers interweaved together to define a fabric transitioning from a single layer to at least two layers corresponding to a balloon transition from a larger diameter central portion to smaller diameter portions on opposite ends of the balloon, wherein the fabric reinforces the balloon while minimizing jamming of the fibers.

6. The medical balloon of claim 5, wherein the central portion defines a cylinder and the smaller diameter portions define cones.

7. The medical balloon of claim 5, wherein the at least two layers each have a same braiding pattern.

8. The medical balloon of claim 5, wherein the single layer has a braiding pattern different than a braiding pattern of the at least two layers.

9. The medical balloon of claim 5, wherein the first and second fibers are disposed to continue without interruption from the single layer to the at least two layers.

10. The medical balloon of claim 5, wherein the single layer has a fiber density twice the fiber density of either of the at least two layers.

11. The medical balloon of claim 5, further comprising a transition line at the balloon transition wherein the single layer divides into the at least two layers.

12. The medical balloon of claim 5, wherein the plurality of first and second fibers together define the single layer.

13. The medical balloon of claim 5, wherein the plurality of first fibers define a first layer of the at least two layers and the plurality of second fibers define a second layer of the at least two layers.

14. The medical balloon of claim 13, wherein the first and second layers may be divided into additional layers at additional transition lines.

15. The medical balloon of claim 1, wherein the fabric has a triaxial structure.

16. The medical balloon of claim 1, wherein the plurality of continuous interwoven fibers are disposed in three directions.

17. The medical balloon of claim 1, wherein the central section is a cylinder and the tapering end is a cone.

18. The medical balloon of claim 1, wherein the single layer has a fiber density twice the fiber density of any layer of the multiple layers.

19. The medical balloon of claim 1, wherein each layer of the multiple layers have an identical braid pattern and are offset relative to each other.

20. The medical balloon of claim 1, further comprising a transition line wherein the single layer divides into the multiple layers.

* * * * *